US011533933B2

(12) United States Patent
Gregg

(10) Patent No.: US 11,533,933 B2
(45) Date of Patent: Dec. 27, 2022

(54) METHODS FOR INCREASING MEAT PRODUCTION IN LIVESTOCK ANIMALS

(71) Applicant: John Malcolm Hall Gregg, Princeton, NJ (US)

(72) Inventor: John Malcolm Hall Gregg, Princeton, NJ (US)

(73) Assignee: John Malcolm Hall Gregg, Princeton, NJ (US)

( * ) Notice: Subject to any disclaimer, the term of this patent is extended or adjusted under 35 U.S.C. 154(b) by 0 days.

(21) Appl. No.: 16/326,446

(22) PCT Filed: Aug. 20, 2017

(86) PCT No.: PCT/US2017/047704
§ 371 (c)(1),
(2) Date: Feb. 19, 2019

(87) PCT Pub. No.: WO2018/039088
PCT Pub. Date: Mar. 1, 2018

(65) Prior Publication Data
US 2021/0386092 A1    Dec. 16, 2021

(51) Int. Cl.
*A23K 10/18* (2016.01)
*A61K 35/741* (2015.01)
*A61K 45/06* (2006.01)
*C12Q 1/02* (2006.01)
*C12Q 1/04* (2006.01)

(52) U.S. Cl.
CPC ............ *A23K 10/18* (2016.05); *A61K 35/741* (2013.01); *A61K 45/06* (2013.01); *C12Q 1/025* (2013.01); *C12Q 1/04* (2013.01)

(58) Field of Classification Search
CPC .................................. C12Q 1/04; A23K 10/18
See application file for complete search history.

(56) References Cited

U.S. PATENT DOCUMENTS 8,951,512 B2 * 2/2015 Blaser ..................... A61P 21/00
424/93.4
2011/0280840 A1 * 11/2011 Blaser ..................... A61P 21/00
424/93.4

OTHER PUBLICATIONS

Davy, A.M., et al. "Cell Factory Engineering", Cell Systems Review, 4(3), pp. 263-275 (Year: 2017).*

* cited by examiner

*Primary Examiner* — Michelle F. Paguio Frising
*Assistant Examiner* — Grant C Currens
(74) *Attorney, Agent, or Firm* — Wiggin and Dana LLP; Anthony D. Sabatelli; Brian A. Pattengale

(57) ABSTRACT

This invention relates to the development of products that are alternatives to antibiotics with medically important human therapeutic uses for livestock meat and protein production efficiency. These products will be used to replace antibiotics used to rapidly increase lean muscle mass with specific feed regimens. The present invention is for the identification of non-human antibiotic products to be used with different feed regimens for livestock growth and meat promotion that include prebiotic supplements and keystone species probiotics that produce the desired growth promotion phenotypic effects. The present invention includes the identification of enterotypes that can be used as targets for recapitulation by compounds that are screened to produce the desired phenotype.

19 Claims, No Drawings

METHODS FOR INCREASING MEAT PRODUCTION IN LIVESTOCK ANIMALS

CROSS-REFERENCE TO RELATED APPLICATIONS

This application is a national phase entry under 35 U.S.C. § 371 of International Application PCT/US2017/047704, filed Aug. 20, 2017, which claims the benefit under 35 U.S.C. § 119(e) of U.S. Provisional Application No. 62/494,765 filed Aug. 20, 2016, all of which are herein incorporated by reference in their entireties.

BACKGROUND

Antibiotics have been used extensively in livestock production species including cattle, swine, poultry, and fish. Antibiotics have been used and approved by regulatory agencies for a variety of purposes including growth promotion, treatment of bacterial diseases, prophylaxis of bacterial disease that is present in the herd or flock of the facility where they are housed, and metaprophylaxis to prevent spread of bacterial disease from nearby sources of infection such as neighboring herds or flocks.

Antibiotics have both health benefits and production efficiency benefits. The health benefits of antibiotics have been the mitigation or cure of bacterial disease that adversely impacts the health of the production species animals. The production efficiency advantages of the antibiotics are that they also promote the gain of lean muscle mass in production species improving both the quality of their meat, increasing the amount of meat at slaughter, decreasing the time needed to gain the optimal amount of weight to optimize meat yield prior to slaughter, and improving the efficiency of weight gain by conversion of feed to energy and deposition of lean body mass. Often, many of these advantages accrue simultaneously. An example would be the use of the macrolide antibiotic, Tylosin, which both promotes growth and also treats liver abscesses caused by anaerobic bacteria, like *Fusobacterium necrophorum*, that sicken cattle and require that the area around the abscesses be cut out with large margins and discarded, reducing the available usable meat for sale.

Since amounts of antibiotics used are based on number of animals to be treated (large numbers to be slaughtered for meat) and the weight of the animals treated (cattle and swine are heavy), which determines dosages used, extensive amounts of antibiotics are used in the various segments of the livestock production industry. Cattle and swine (hogs) are big animals that require large absolute amounts of antibiotics to be used to reach minimum inhibitory concentrations to modulate bacteria populations in their GI microbiomes for the desired weight gain phenotypic effect. Poultry species, like chickens and turkeys, and fish are raised in huge numbers of animals to meet demand for meat. The absolute numbers of animals used meat production of these animals requires large absolute amounts of antibiotics to be used even though the amount per animal is less.

The amounts of antibiotics (in tons) used are large, even when growth promotion and prophylactic/metaprophylactic use of these products are at a lower dosage (one half or one quarter) of the dosages used for antibacterial therapeutics purposes.

There is concern in the human infectious disease academic community that large absolute amounts of antibiotics used in livestock production could apply selective pressure on bacterial species that could lead to the development of resistance of medically important human antibiotics if resistance genes arising in the livestock production setting were to be able to cross over into human populations through xenobiotic transfer into the immunocompromised human hospital population, general population, or general population through the food supply chain.

As a result of these concerns about the development of antibiotic resistance to key human antibiotics, the low rate of discovery of new antibiotics & development of them into commercially available products, and the dwindling number of antibiotics for which no significant levels of resistance have already developed, the government and private sectors are encouraging antibiotic stewardship programs designed to extend the useful life of antibiotics and slow the development of resistance.

Some of these antibiotic stewardship initiatives include the reduction or elimination of the use of antibiotics in livestock production systems. This is one of the initiatives in President Obama's "CARB" (Combating antimicrobial resistant bacteria) program that was introduced in 2015 along with the phased implementation of the Food & Drug Administration's (FDA's) Veterinary Feed Directive (VFD). The CARB National Action Plan called for the development of alternatives to antibiotics in livestock production systems.

The present invention provides alternatives to antibiotics in livestock production systems and is needed to fulfil the same purpose of maintaining health and increasing production efficiency in these animals. It contains a process for identifying bacterial enterotypes that that result in efficient conversion of feed (specific recipes) to the deposition of lean body muscle and lean mass with high meat quality through the modulation of keystone bacterial species up and down for optimization of their compositional diversity and relative abundance in target compartments of the gastrointestinal system including rumen/stomach, small intestines, and colon.

Antibiotics mostly reversibly change the microbiome in the hosts in whom they are adminstered. The changes induced by the antibiotics, based on their individual spectrums of activity, are in compositional diversity & taxonomy, and in their relative abundance in different GI microbiome present in various compartments.

Mechanisms of bacterial resilience, including the germination of previously environmentally released spores that are ingested, as well as planktonic bacteria shed from biofilm reservoirs, restore the original microbiome long after antibiotics have been discontinued. In some cases the resilience will restore a homeostasis that was reached prior to events that caused a dysbiosis with bacterial overgrowth of particular species, or strains of those species. This resilience and restoration of previous equilibrium can also arrest continuing phenotypic effects from antibiotic administration, including weight gain by the deposition of lean muscle mass that has been observed with continuous administration of regular dose, or low dose, antibiotics over time.

As a result, the enterotypes associated with livestock production species growth promotion may have to be maintained with long term administration of bacterial species (probiotics), or the use of prebiotics that stabilize these patterns and their associated phenotypic effects of growth promotion and deposition of lean muscle mass.

While at least 13 different classes of antibiotics, all with different spectrums of antibacterial activity, have been used in the main types of food production species (cattle, swine, poultry, and fish), to promote production efficiency, none of their enterotypes associated with specific feed regimens have been systematically studied and characterized, and thus the metabolic solutions (combinations of metabolic products of key microbiota species and strains) have not been previously described in detail following metabolomic analysis, nor have metabolic products in the form of probiotics (live bacterial therapeutics) or prebiotics, been developed to produce the same phenotypic effects of the antibiotic modulated enterotypes.

Keystone species of bacteria involved with the promotion or inhibition of deposition of lean muscle mass in the various production species (cattle, swine, poultry, and fish) have not previously been systematically identified by antibiotic associated enterotype and used to produce translational products that either are produced by these systems or by products that have been screened to have the effect of recapitulating these effects on weight gain and lean body mass deposition.

SUMMARY OF THE INVENTION

The present invention is a set of compositions for more quickly producing lean muscle mass in livestock species, rather than fat, and the processes and methods of developing these compositions.

The present invention includes compositions that are administered in feed and/or in water to livestock that are metabolic solutions (hereby defined as "Bolsols") for digesting different feeds and optimizing their energy conversion for the animal and its deposition of lean muscle mass that provides a high meat quality. These compositions are artificially derived subsets and mixtures of metabolic products that come from larger metabolic solution recipes encoded in the genomes of unique sets of microbiota combined with genomes of the host livestock species (known as the "hologenome of the holobiome").

The compositions in the present invention are made up components that include, but are not limited to, particular vitamins (e.g., $K_1$), proteins e.g., trypsin), fatty acids (including short chain fatty acids like butyrate), and sugars (e.g., glucose), in specific set of combinations, as well as compounds screened to modulate microbiota in various gastrointestinal microbiomes (e.g. those found in the stomachs, small intestines, & colons) of livestock species to produce these component combinations with the desired phenotypic effect of deposition of lean muscle mass.

In a specific embodiment, these compositions are developed for co-administration with feeds for beef cattle.

In a specific embodiment, these compositions are developed for co-administration with feeds for dairy cattle.

In a specific embodiment, these compositions are developed for co-administration with feeds for broiler chickens.

In a specific embodiment, these compositions are developed for co-administration with feeds for egg laying chickens.

In a specific embodiment, these compositions are developed for co-administration with feeds for turkeys.

In a specific embodiment, these compositions are developed for co-administration with feeds for farmed fish including, but not limited to salmon, catfish, tilapia, trout, and tuna.

In a specific embodiment, these compositions are developed for co-administration with feeds for swine.

In a specific embodiment, these compositions are developed for co-administration with feeds for bison.

In a specific embodiment, these compositions are developed for co-administration with feeds for venison.

In a specific embodiment, these compositions are developed for co-administration with feeds for sheep mutton and lamb.

In a specific embodiment, these compositions are developed for co-administration with feeds for goats.

The present invention includes a process for determining the optimized components of the metabolic solutions for particular types of livestock feed. This process consists of determining the metabolic solutions for the type of feed in combination with an antibiotic in one of thirteen different classes demonstrated to alter the dimensions of compositional diversity in different gastrointestinal microbiomes of the livestock species including those in the stomach (or rumen), small intestines, and colon.

In a specific embodiment, enterotypes associated with specific feeds are determined by the present invention after administration of aminoglycoside antibiotics.

In another specific embodiment, enterotypes associated with specific feeds are determined by the present invention after administration of cephalosporin antibiotics.

In another specific embodiment, enterotypes associated with specific feeds are determined by the present invention after administration of cyclic peptides.

In another specific embodiment, enterotypes associated with specific feeds are determined by the present invention after administration of diterpines.

In another specific embodiment, enterotypes associated with specific feeds are determined by the present invention after administration of hydrazines.

In another specific embodiment, enterotypes associated with specific feeds are determined by the present invention after administration of ionophores.

In another specific embodiment, enterotypes associated with specific feeds are determined by the present invention after administration of lincosamides.

In another specific embodiment, enterotypes associated with specific feeds are determined by the present invention after administration of macrolides.

In another specific embodiment, enterotypes associated with specific feeds are determined by the present invention after administration of organoarsenics.

In another specific embodiment, enterotypes associated with specific feeds are determined by the present invention after administration of penicillin.

In another specific embodiment, enterotypes associated with specific feeds are determined by the present invention after administration of streptogramins.

In another specific embodiment, enterotypes associated with specific feeds are determined by the present invention after administration of sulfonamides.

In another specific embodiment, enterotypes associated with specific feeds are determined by the present invention after administration of tetracyclines.

In another specific embodiment, enterotypes associated with specific feeds are determined by the present invention after administration of coccidiostats.

The process and methods in the present invention for determining the optimized components of the metabolic solutions for particular types of livestock feed is to ascertain by experiment in feedlot type of experimental facilities the shifts in dimensions of compositional diversity and relative abundance of microbiota involved in feed digestion by co-administration with feed of an antibiotic in an identified class and then analyzing both cross-sectionally and longitudinally the results, using metagenomic, transcriptomics, proteomics, and metabolomics. These shifts in dimensions of compositional diversity and relative abundance represented by specific enterotype patterns discovered by this process are then recapitulated in their key components by administration of keystone metabolic end products as prebiotics, or by administration of keystone species as probiotics which serve as biological factories for production of these metabolic end products that demonstrate the phenotypic effect of deposition of lean muscle rather than fat.

In another specific embodiment, the present invention includes compounds and/or drugs that have been screened to recapitulate the target enterotype that exhibits the desired phenotypic effect of deposition of lean muscle rather than fat which are administered as prebiotics to production livestock species including cattle, poultry (including raised game birds), swine, fish (including farmed fish), venison, bison, sheep, and goats.

DETAILED DESCRIPTION OF THE INVENTION

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Where appropriate, any one or more of the other active agents may be in the form of a pharmaceutically acceptable salt.

Suitable pharmaceutically acceptable salts include, but are not limited to, salts of pharmaceutically acceptable inorganic acids such as hydrochloric, sulfuric, phosphoric, nitric, carbonic, boric, sulfuric, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

It is intended that the aspects and embodiments of this invention encompasses all solid forms, including amorphous forms, as well as crystalline forms, and polymorphs thereof.

Throughout this specification the term 'in combination' means that one or more other actives are both administered to the fish or livestock animal over the same period of treatment. They may be administered together, i.e. at the same time. In this case they may be administered in a single formulation, (e.g. as a single tablet or capsule or feed pellets) or in separate formulations administered simultaneously or nearly simultaneously in feed or water or milled feed combination, or probiotic with colony formation units (CFUs) deposited on feed. Alternatively, they may be administered at separate times of day.

The combinations of the invention provide benefits which are at least additive compared to the use of either agent alone. In many embodiments, the combinations are something more than additive, e.g. synergistic, compared to the use of either agent alone.

The definition of the term 'treatment' in this specification encompasses both growth promotion and deposition of lean muscle mass for production efficiency as well as this purpose plus disease treatment, prophylaxis and prevention (i.e. reducing or eliminating the risk of contracting the disease). As well as meaning curing animals of the disease, 'treatment' also includes preventing the onset of symptoms, controlling (e.g. by slowing or eliminating) progression of disease, preventing the spread of the disease to other parts of the body and/or to other persons, reducing the spread of the disease and other facets of veterinary practice which will be readily understood by the person skilled in the art to fall within the meaning of the term 'treatment'.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

FORMULATIONS

For the above-mentioned therapeutic uses, the dosage administered will, of course, vary with the compound employed, the mode of administration, the treatment desired and the production purpose or disorder indicated.

Compositions may be administered systemically, e.g. by oral administration in the form of mixed or milled feeds, tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

For oral administration, one or more active agents may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, one or more active agents may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules. Liquid preparations for oral application may be in the form of sprayed depositions on solid feeds, syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

Methods of Bioinformatics

The bioinformatics of the present invention employs for metagenomic microbiota analysis a base of both 16S ribosomal RNA fingerprinting as well as whole genome shotgun sequencing (WGS) analysis of metagenomic data. The WGS in the present invention includes techniques that use iterative scanning of small motifs, including 12 amino-acid (36 bp) motifs, that are then compared for a comprehensive taxonomy against all 280,000 named organisms in public databases and are benchmarked against other pipelines (e.g., MetaPhlan, Phylosift, GOTTCHA and Kraken).

The present invention includes metagenomic, proteomic, transcriptomic, and metabolomic analyses of the various GI microbiomes (e.g., stomach, rumen, small intestines, colon) for each livestock production species, including, but not limited to cattle, poultry (including raised game birds), swine, fish (including farmed fish), venison, bison, sheep, and goats, both before and after administration of an antibiotic, including, but not limited to, those in the class of aminoglycosides, cephalosporins, cyclic peptides, diterpines, fluoroquinolones, hydrazines, ionophores, lincosamides, macrolides, organoarsenics, nitroimidazoles, penicillins, streptogramins, and sulfonamides in combination with various feeds used for those production species.

The present invention also includes metagenomic, proteomic, transcriptomic, and metabolomic analyses of the various GI microbiomes (e.g., stomach, rumen, small intestines, colon) for each livestock production species, including, but not limited to cattle, poultry (including raised game birds), swine, fish (including farmed fish), venison, bison, sheep, and goats, both before and after administration of combinations of antibiotics, including, but not limited to, those in the class of aminoglycosides, cephalosporins, cyclic peptides, diterpines, fluoroquinolones, hydrazines, ionophores, lincosamides, macrolides, organoarsenics, nitroimidazoles, penicillins, streptogramins, and sulfonamides in combination with various feeds used for those production species.

The present invention also includes metagenomic, proteomic, transcriptomic, and metabolomic analyses of the various GI microbiomes (e.g., stomach, rumen, small intestines, colon) for each livestock production species, including, but not limited to cattle, poultry (including raised game birds), swine, fish (including farmed fish), venison, bison, sheep, and goats, both before and after administration of combinations of antibiotics and antiprotozoal agents, including, but not limited to, those in the class of coccidiostats, aminoglycosides, cephalosporins, cyclic peptides, diterpines, fluoroquinolones, hydrazines, ionophores, lincosamides, macrolides, organoarsenics, nitroimidazoles, penicillins, streptogramins, and sulfonamides in combination with various feeds used for those production species.

The present invention includes the different enterotypes (including their use as informational recipes) associated with feed regimens determined by metagenomic analysis of the various GI microbiomes (e.g., stomach, rumen, small intestines, colon) for each livestock production species, including, but not limited to cattle, poultry (including raised game birds), swine, fish (including farmed fish), venison, bison, sheep, and goats, both before and after administration of an antibiotic, including, but not limited to, those in the class of aminoglycosides, cephalosporins, cyclic peptides, diterpines, fluoroquinolones, hydrazines, ionophores, lincosamides, macrolides, organoarsenics, nitroimidazoles, penicillins, streptogramins, and sulfonamides used for those production species.

The present invention also the different enterotypes (including their use as informational recipes) associated with feed regimens determined by metagenomic analysis of the various GI microbiomes (e.g., stomach, rumen, small intestines, colon) for each livestock production species, including, but not limited to cattle, poultry (including raised game birds), swine, fish (including farmed fish), venison, bison, sheep, and goats, both before and after administration of combinations of antibiotics, including, but not limited to, those in the class of aminoglycosides, cephalosporins, cyclic peptides, diterpines, fluoroquinolones, hydrazines, ionophores, lincosamides, macrolides, organoarsenics, nitroimidazoles, penicillins used for those production species.

The present invention also includes the different enterotypes (including their use as informational recipes) associated with feed regimens determined by metagenomic analysis of the various GI microbiomes (e.g., stomach, rumen, small intestines, colon) for each livestock production species, including, but not limited to cattle, poultry (including raised game birds), swine, fish (including farmed fish), venison, bison, sheep, and goats, both before and after administration of combinations of antibiotics and antiprotozoal agents, including, but not limited to, those in the class of coccidiostats, aminoglycosides, cephalosporins, cyclic peptides, diterpines, fluoroquinolones, hydrazines, ionophores, lincosamides, macrolides, organoarsenics, nitroimidazoles, penicillins, streptogramins, and sulfonamides used for those production species.

The present invention includes the keystone species in enterotypes, and products derived from their administration or administration of their metabolic products, determined by comparison of the metagenomic, proteomic, transcriptomic, and metabolomic analyses of the various GI microbiomes (e.g., stomach, rumen, small intestines, colon), analysed in sequence of the passage of food in the digestive tract (first stomach or rumen, then small intestines, then colon) of the different livestock production species, including, but not limited to cattle, poultry (including raised game birds), swine, fish (including farmed fish), venison, bison, sheep, and goats, both before and after administration of an antibiotic, including, but not limited to, those in the class of aminoglycosides, cephalosporins, cyclic peptides, diterpines, fluoroquinolones, hydrazines, ionophores, lincosamides, macrolides, organoarsenics, nitroimidazoles, penicillins, streptogramins, and sulfonamides in combination with various feeds used for those production species, to determine a metabolic code for digestion through the solving of simultaneous equations with variables being bacterial strains with genes encoding metabolic products for food breakdown.

The present invention encompasses combinations of enterotype probiotic products or artificially optimized metabolic solutions (Bolsols) that are non-naturally occurring.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification, or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A method for depositing lean muscle in livestock animals comprising the steps of:

determining one or more natural bacterial enterotypes of a livestock;
administering one or more antibiotics to the livestock;
identifying one or more antibiotic administration-induced bacterial enterotypes;
comparing the antibiotic administration-induced bacterial enterotypes to the natural bacterial enterotypes to identify one or more keystone bacterial species;
defining a composition comprising a probiotic containing at least one of the keystone bacterial species or a prebiotic containing prebiotic metabolic products produced by said keystone bacterial species, for administration to the livestock; and
administering the composition to the livestock,
wherein said administration of the composition results in the phenotypic effect of deposition of lean muscle rather than fat in the livestock.

2. The method of claim 1 wherein each of the bacterial enterotypes represent the gastrointestinal microbiomes in one or more of the stomach, rumen, small intestines, or colon.

3. The method of claim 1, wherein the one or more antibiotics are selected from the group consisting of aminoglycosides, cephalosporins, cyclic peptides, diterpenes, fluoroquinolones, hydrazines, ionophores, lincosamides, macrolides, organoarsenics, nitroimidazoles, penicillins, streptogramins, and sulfonamides.

4. The method of claim 1, wherein the one or more antibiotics are co-administered with a feed regimen.

5. The method of claim 1, wherein the livestock is selected from the group consisting of cattle, poultry, swine, fish, sheep, goat, deer, and bison.

6. The method of claim 1, wherein each enterotype is determined by one or more of metagenomic, proteomic, transcriptomic, and metabolomic analyses.

7. The method of claim 1, wherein the one or more keystone bacterial species are associated with the phenotypic effect of deposition of lean muscle rather than fat.

8. The method of claim 1 wherein administration of the probiotic produces metabolic end products that result in the phenotypic effect of deposition of lean muscle rather than fat when administered to the livestock.

9. The method of claim 1, wherein the prebiotic metabolic products are produced by the at least one keystone bacterial species used as a biological factory in a bioreactor.

10. The method of claim 1, wherein the one or more enterotypes identified include one or more of the gastrointestinal microbiomes of the stomach, rumen, small intestines, and colon.

11. A method for depositing lean muscle in a livestock animal comprising the steps of:
determining a natural bacterial enterotype of a livestock;
administering one or more antibiotics to the livestock to yield a desired phenotype;
identifying one or more antibiotic administration-induced target bacterial enterotypes associated with the desired phenotype;
screening for one or more non-antibiotic compounds that recapitulate the target bacterial enterotypes; and
administering the one or more non-antibiotic compounds as a prebiotic to the livestock, wherein the administration of the prebiotic results in deposition of lean muscle rather than fat in the livestock.

12. The method of claim 11, wherein the one or more antibiotics are selected from the group consisting of aminoglycosides, cephalosporins, cyclic peptides, diterpenes, fluoroquinolones, hydrazines, ionophores, lincosamides, macrolides, organoarsenics, nitroimidazoles, penicillins, streptogramins, and sulfonamides.

13. The method of claim 11 wherein the bacterial enterotype represents the gastrointestinal microbiome in one or more of the stomach, rumen, small intestines, or colon.

14. The method of claim 11 wherein the desired phenotype is deposition of lean muscle rather than fat in the livestock.

15. The method of claim 11 wherein the livestock is selected from the group consisting of cattle, poultry, swine, fish, sheep, goat, deer, and bison.

16. The method of claim 11, wherein the one or more enterotypes identified include one or more of the gastrointestinal microbiomes of the stomach, rumen, small intestines, and colon.

17. A screening-based method for producing lean muscle in a livestock animal comprising the steps of:
determining a natural bacterial enterotype of a livestock;
administering one or more antibiotics to the livestock to yield a desired phenotype;
identifying one or mores antibiotic administration-induced target bacterial enterotypes associated with the desired phenotype;
screening for one or more non-antibiotic compounds that recapitulate the target bacterial enterotypes; and
administering the one or more non-antibiotic compounds to obtain the desired phenotype, wherein the desired phenotype is deposition of lean muscle rather than fat in the livestock.

18. The method of claim 17 wherein the non-antibiotic compounds are administered in a tablet, in feed pellets, in a formulation administered simultaneously or nearly simultaneously in feed, water, or milled feed combination, in a probiotic with colony formation units deposited on feed, or in a formulation administered at separate times of day from feed.

19. The method of claim 17, wherein the one or more enterotypes identified include one or more of the gastrointestinal microbiomes of the stomach, rumen, small intestines, and colon.

* * * * *